(12) United States Patent
Guo et al.

(10) Patent No.: US 10,322,172 B2
(45) Date of Patent: Jun. 18, 2019

(54) LIVE, ATTENUATED VACCINES AND METHODS OF MAKING AND USING

(71) Applicant: NUtech Ventures, Lincoln, NE (US)

(72) Inventors: Jiantao Guo, Lincoln, NE (US); Qingsheng Li, Lincoln, NE (US); Wei Niu, Lincoln, NE (US); Yue Li, Lincoln, NE (US); Nanxi Wang, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 0 days.

(21) Appl. No.: 15/117,949

(22) PCT Filed: Feb. 10, 2015

(86) PCT No.: PCT/US2015/015229
§ 371 (c)(1),
(2) Date: Aug. 10, 2016

(87) PCT Pub. No.: WO2015/120459
PCT Pub. Date: Aug. 13, 2015

(65) Prior Publication Data
US 2016/0375128 A1    Dec. 29, 2016

Related U.S. Application Data

(60) Provisional application No. 61/937,712, filed on Feb. 10, 2014.

(51) Int. Cl.
| A61K 39/12 | (2006.01) |
| A61K 39/21 | (2006.01) |
| C12N 7/00 | (2006.01) |
| A61K 39/00 | (2006.01) |

(52) U.S. Cl.
CPC .............. *A61K 39/21* (2013.01); *A61K 39/12* (2013.01); *C12N 7/00* (2013.01); *A61K 2039/5254* (2013.01); *C12N 2740/16021* (2013.01); *C12N 2740/16034* (2013.01); *C12N 2740/16051* (2013.01); *C12N 2740/16234* (2013.01)

(58) Field of Classification Search
None
See application file for complete search history.

(56) References Cited

U.S. PATENT DOCUMENTS

| 6,033,902 A * | 3/2000 | Haseltine ............. C07K 14/005 435/235.1 |
| 2013/0323821 A1* | 12/2013 | Tian ........................ C12N 1/36 435/252.33 |

OTHER PUBLICATIONS

Kohl et al. Active human immunodeficiency virus protease is required for viral infectivity. PNAS, Jul. 1988, vol. 85, No. 13, pp. 4686-4690.*
Chatterjee et al. Efficient viral delivery system for unnatural amino acid mutagenesis in mammalian cells. Proc. Natl. Assoc. Sci. 2013; 110(29): 11803-11808.*
AAP85289, 2016.*
AY324226, 2016.*
Chen et al., "A Facile System for Encoding Unnatural Amino Acids in Mammalian Cells," Angew. Chem. Int. Ed., 2009, 48:4052-55.
(Continued)

*Primary Examiner* — Janet L Andres
*Assistant Examiner* — Stuart W Snyder
(74) *Attorney, Agent, or Firm* — Fish & Richardson P.C.

(57) ABSTRACT

A live, attenuated HIV vaccine is provided, and methods of making a attenuated HIV vaccine are provided.

18 Claims, 12 Drawing Sheets
Specification includes a Sequence Listing.

Tissue Culture Infectious Dose 50 (TCID50/ml)

| wt pSUMA | pSUMA-Tyr59 | pSUMA-Trp36Gln127 |
|---|---|---|
| $5.10 \times 10^3$ | $1.31 \times 10^3$ | $5.12 \times 10^3$ |

(56) References Cited

OTHER PUBLICATIONS

International Preliminary Report on Patentability in International Application No. PCT/US2015/015229, dated Aug. 16, 2016, 8 pages.
International Search Report and Written Opinion in International Application No. PCT/US2015/15229, dated Oct. 1, 2015, 18 pages.
Kohl et al., "Active human immunodeficiency virus protease is required for viral infectivity," PNAS, Jul. 1988, 85(13): 4686-4690.
Liu et al., "Genetic incorporation of unnatural amino acids into proteins in mammalian cells," Nat. Methods, 2007, 4:239-44.
Niu et al., An Expanded Genetic Code in Mammalian Cells With a Functional Quadruplet Codon, ACS Chem. Biol., Jul. 2013, 8:1640-5.
Wang et al., "Genetically encoding unnatural amino acids for cellular and neuronal studies," Nat. Neurosci., Aug. 2007, 10:1063-72.

* cited by examiner

Normalized absorbance (450 nm) values of above p24 assays

| A-1   | A-3   | A-5    | A-7    | A-9   | A-11  |
|-------|-------|--------|--------|-------|-------|
| 6.181 | 0.001 | 8.854  | -0.010 | 3.920 | 0.000 |
| A-2   | A-4   | A-6    | A-8    | A-10  | A-12  |
| 6.778 | 0.453 | -0.010 | 2.127  | 3.608 | 0.785 |

| wt pSUMA | pSUMA-Tyr59 | pSUMA-Trp36Gln127 |
| --- | --- | --- |
| A | B | C |

Tissue Culture Infectious Dose 50 (TCID50/ml)

| wt pSUMA | pSUMA-Tyr59 | pSUMA-Trp36Gln127 |
| --- | --- | --- |
| $5.10 \times 10^3$ | $1.31 \times 10^3$ | $5.12 \times 10^3$ |

FIG. 5

Normalized OD values of above p24 assays

| well 1 | well 4 | well 7 |
|---|---|---|
| 6.181 | 7.262 | 0.003 |
| well 2 | well 5 | well 8 |
| 0.000 | 1.364 | -0.009 |
| well 3 | well 6 | well 9 |
| 0.785 | 3.201 | 1.912 |

US 10,322,172 B2

SEQUENCE LISTING

```
<160> NUMBER OF SEQ ID NOS: 23

<210> SEQ ID NO 1
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1
ctagaacgat tcgcagttaa ccctg                                           25

<210> SEQ ID NO 2
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 2
gttctgcact ataggctaat tttggctgac ctggctg                              37

<210> SEQ ID NO 3
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 3
tagcctatag tgcagaacct ccag                                            24

<210> SEQ ID NO 4
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 4
gtgcctatag ctttgtgtcc acag                                            24

<210> SEQ ID NO 5
<211> LENGTH: 25
<212> TYPE: DNA
<213> ORGANISM: Artificial Sequence
<220> FEATURE:
```

<223> OTHER INFORMATION: synthetic oligonucleotide

<400> SEQUENCE: 5
ctagaacgat tcgcagttaa ccctg                                     25

<210> SEQ ID NO 6
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 6
tttcctgcgt cagcctatgc ttgctgtgct tttttcttac                     40

<210> SEQ ID NO 7
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 7
ctgacgcagg aaacaacagc cag                                       23

<210> SEQ ID NO 8
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 8
gtgcctatag ctttgtgtcc acag                                      24

<210> SEQ ID NO 9
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 9
caaagtaaga caatatgatc aggtaac                                   27

<210> SEQ ID NO 10
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 10
cacctctaca gatgttctct cagttcctc                                 29

<210> SEQ ID NO 11
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 11
catctgtaga ggtggggatt taccacac                                  28

<210> SEQ ID NO 12
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 12
gcttcccatg tttctctttg tatg					24

<210> SEQ ID NO 13
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 13
ctagaacgat tcgcagttaa ccctg					25

<210> SEQ ID NO 14
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 14
atttctatgg ttacctgatc ctattgtctt actttgataa aac					43

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
gtagaggatc cactagtaac					20

<210> SEQ ID NO 16
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 16
tagctccctg cttgcctata ctatatgttt taattg					36

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 17
ggcaagcagg gagctagaac					20

<210> SEQ ID NO 18
<211> LENGTH: 24
<212> TYPE: DNA

```
<213> ORGANISM: Artificial Sequence
<220> FEATURE:
<223> OTHER INFORMATION: synthetic oligonucleotide

<400> SEQUENCE: 18
gtgcctatag ctttgtgtcc acag                                              24

<210> SEQ ID NO 19
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 19
gctataagac gcgtccacca tg                                                22

<210> SEQ ID NO 20
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 20
cctaggtggc atcgccctc                                                    19

<210> SEQ ID NO 21
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 21
cgatgccacc tagggaaagc tgaccctgaa gttc                                   34

<210> SEQ ID NO 22
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 22
cgtctagatt acttgtacag ctcatc                                            26

<210> SEQ ID NO 23
<211> LENGTH: 16
<212> TYPE: PRT
<213> ORGANISM: Artificial Sequence
<220> FEATURE:
<223> OTHER INFORMATION: synthetic peptide

<400> SEQUENCE: 23

Phe Ser Val Ser Gly Glu Gly Glu Gly Asp Ala Thr Ala Phe Gly Lys
1               5                   10                  15
```

LIVE, ATTENUATED VACCINES AND METHODS OF MAKING AND USING

CROSS REFERENCE TO RELATED APPLICATIONS

This application is a National Stage Application under 35 U.S.C. § 371 and claims the benefit of International Application No. PCT/US2015/015229, filed Feb. 10, 2015, which claims the benefit of priority under 35 U.S.C. § 119(e) to U.S. Application No. 61/937,712, filed on Feb. 10, 2014.

TECHNICAL FIELD

This disclosure generally relates to vaccines.

BACKGROUND

Historically, vaccines have been the best weapon against the world's deadliest infectious diseases, including smallpox, polio, and yellow fever. Live, attenuated vaccines in general tend to elicit the most potent protective immunity, since it is the closest mimic of a natural infection. Therefore, live, attenuated vaccines elicit strong protective cellular and antibody responses and often confer a lifelong immunity with only one or two dosings.

This disclosure provides a novel method for producing live-attenuated therapeutic vaccines against a wide array of pathogenic viruses or bacteria.

SUMMARY

A live, attenuated vaccine is provided, and methods of making a live, attenuated vaccine are provided.

In one aspect, a live, attenuated HIV vaccine is provided, where the genome of the HIV includes at least one first mutation in an essential region. Typically, the first mutation is a nonsense mutation.

In some embodiments, the genome of the HIV further comprises at least one transgene in a non-essential region, the transgene encoding a suppressor tRNA and a corresponding aminoacyl-tRNA synthetase.

In some embodiments, the genome of the HIV further comprises at least one second mutation in an essential region. Typically, the second mutation results in a codon encoding for an unnatural amino acid. In some embodiments, the unnatural amino acid is a photoreactive amino acid such as, for example, a photocaged amino acid (e.g., ONBK and ONBY).

In some embodiments, the essential region is the gag gene or the protease gene. In some embodiments, the non-essential region is between the env gene and the nef gene.

In another aspect, a method of making a live, attenuated HIV vaccine is provided. Such a method generally includes infecting a host cell with a live, attenuated HIV vaccine as described herein; and purifying the live, attenuated HIV vaccine.

In some embodiments, the method further can include exposing the infected host cell to light. In some embodiments, the light is UV light (e.g., 365 nm light).

In some embodiments, the host cell includes at least one transgene encoding the suppressor tRNA and the corresponding aminoacyl-tRNA synthetase.

In yet another aspect, an article of manufacture for producing a live, attenuated HIV vaccine is provided. Generally, such an article of manufacture includes a live, attenuated HIV vaccine as described herein; and at least one unnatural amino acid (UAA*).

In some embodiments, the article of manufacture further can include a host cell.

In some embodiments, the host cell includes and expresses at least one transgene encoding a first suppressor tRNA and a first corresponding aminoacyl-tRNA synthetase pair that recognizes the unnatural amino acid.

In some embodiments, an article of manufacture further can include a photoreactive amino acid. In some embodiments, the UAA* is a photoreactive amino acid.

In some embodiments, the host cell further includes at least one transgene encoding a second suppressor tRNA and a second corresponding aminoacyl-tRNA synthetase pair that recognizes the photoreactive amino acid.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 5 is data showing infection assays with TZM-b1 cells. Panel (A) shows cells infected with wild-type pSUMA; Panel (B) shows cells infected with pSUMA-Tyr59; Panel (C) shows cells infected with pSUMA-Trp36Gln127. Scale bars, 200 μm. The doses used for infection are shown as Tissue Culture Infectious Dose 50 (TCID50). The wild-type pSUMA was diluted 4-fold and the pSUMA mutants were concentrated 15-fold in order to adjust the infectious dose of each variant to a similar level.

DETAILED DESCRIPTION

Genetic code expansion with evolved orthogonal suppressor tRNA-aminoacyl-tRNA synthetase (aaRS) pair has been widely applied to the site-specific incorporation of unnatural amino acids (UAA*s) having unique chemical and physical properties into proteins in living cells to facilitate the study of protein structure and function. This disclosure provides a new application for genetic code expansion that couples a UAA*-mediated blank codon (i.e., a codon that does not encode a natural proteinogenic amino acid) suppression of the virus assembly process in the development of a live, attenuated vaccine. Using this strategy, replication of the infectious agent can be precisely controlled by UAA*s, thereby creating a live, attenuated vaccine.

Figure 1A:
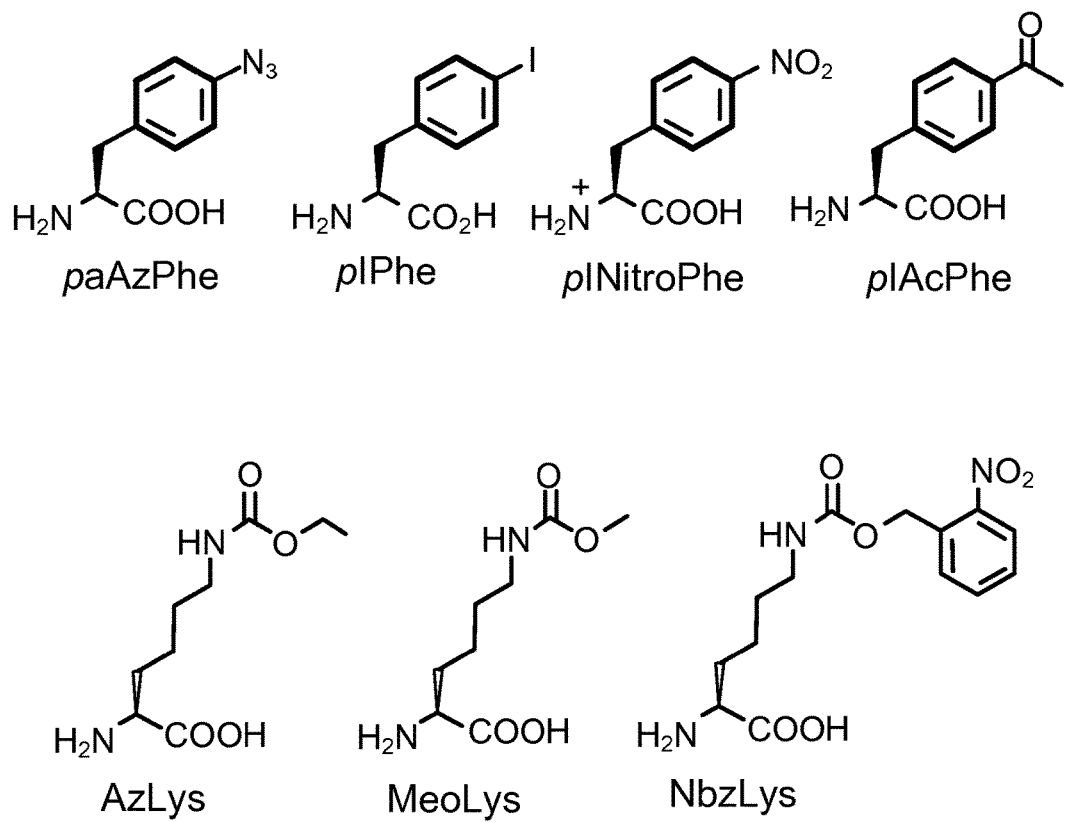
FIG. 1 is a schematic showing the use of blank codons to control HIV replication. Panel A is the structure of representative unnatural amino acids (UAA*); and Panel B is a schematic showing how the replication of HIV is controlled using blank codons and UAA*s.
Figure 1B:
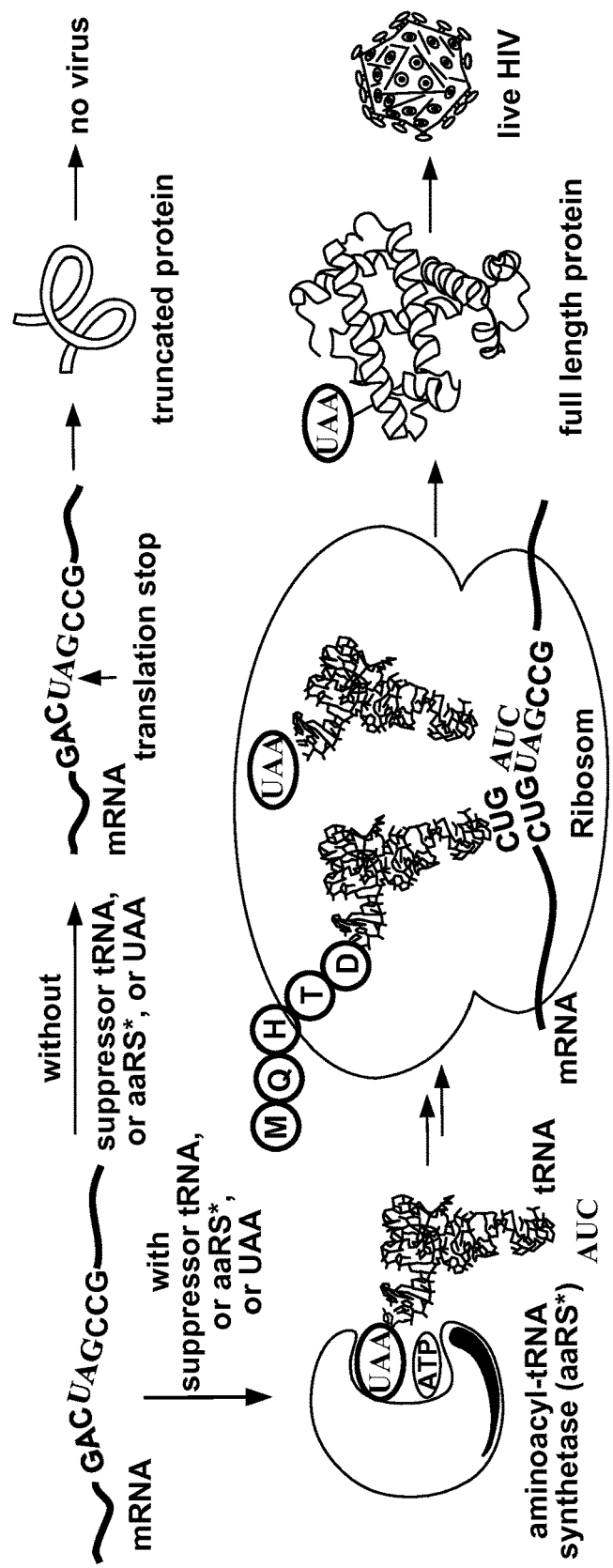

This disclosure describes the use of an unnatural amino acid (UAA*)-mediated blank codon suppression system (FIG. 1). It is demonstrated herein that introducing blank codons within essential regions of the HIV genome can prevent the proper translation and assembly of viable virus particles. However, live and functional HIV particles can be assembled in the presence of a special tRNA-aminoacyl-tRNA synthetase pair that is able to decode the blank codon. The assembled virus particles can be used as a live, attenuated vaccine. Since the host does not contain the special tRNA-aminoacyl-tRNA synthetase pair, the virus can undergo only one cycle of infection and is not able to replicate, which attenuates the virus. To make the system as stringent as possible, specific tRNA-aminoacyl-tRNA synthetase pairs that only recognize unique UAAs* are used. In other words, the unique UAA*s are not present in the host and, preferably, are not present in nature. The UAA*-mediated blank codon suppression system described herein provides the ability to turn on and off replication cycles of the virus in vivo using UAA* as the control element.

While the fidelity of UAA* incorporation is generally comparable to the fidelity of amino acid incorporation in nature, the possibility remains that the virus could regain functional replication by mutating a nonsense codon back to a sense codon given the high genetic variability exhibited by HIV and viruses in general. Thus, the introduction of more than one nonsense codon (e.g., two nonsense codons, three nonsense codons, four nonsense codons) into one or more essential regions (e.g., two different essential regions) of the virus can increase the control over virus replication. Simply by way of example, if the virus mutation rate is assumed to be approximately $3\times10^{-5}$ per nucleotide per cycle of replication (Rambaut et al., 2004, Nat. Rev. Genet., 5:52-61) and the virus life cycle is assumed to be one day, the possibility of mutating one or two nonsense codons back to sense codons is approximately 1% and 0.01%, respectively, within the human life span (for purposes herein, assumed to be 100 years). In addition, nonsense mutations can be introduced into essential regions that exhibit a lower mutation rate, even further reducing the likelihood that a mutant would regain virulence.

While HIV was used herein to exemplify the methods, a similar approach also can be used to generate or improve the safety of live, attenuated vaccines for any number of infectious viruses or bacteria.

Live, Attenuated Vaccines and Methods of Making

The sequence of the human immunodeficiency virus (HIV) genome is known and can be found at GenBank Accession No. AF033819.3. HIV includes two copies of non-covalently linked, un-spliced, positive-sense single-stranded RNA enclosed by a conical capsid. The RNA component is less than 10 kb (i.e., 9749 nucleotides in length) and the nucleocapsid associates with the genomic RNA (one molecule per hexamer) to protect the RNA from attach by nucleases.

The HIV genome encodes a number of essential structural proteins including the group-specific antigen (gag) protein, the polymerase (pol) protein, and the envelope (env) protein. The gag gene encodes the precursor Gag polyprotein that is processed by the viral protease during maturation. The pol gene encodes the reverse transcriptase and RNase H enzymes, which are required to produce DNA from the RNA template, as well as an integrase and a protease. The integrase is required to integrate the double-stranded viral DNA into the host genome, and the protease is required to cleave the precursor Gag polyprotein to produce some of the structural proteins. The env gene encodes gp160, which is cleaved by a host protease and results in a surface glycoprotein that ultimately embeds in the viral envelope and enables the virus to attach to and fuse with target cells.

The HIV genome also contains several essential regulatory elements including the HIV trans-activator (tat) and the regulator of expression of virion proteins (rev). The tat protein plays an important role early in HIV infection in regulating the reverse transcription of viral genome RNA, ensuring efficient synthesis of viral mRNAs and regulating the release of virions from infected cells. Given its role in infection and transcription, the tat protein is essential for the survival of HIV. The rev protein binds to the viral genome via an arginine-rich RNA-binding motif that also acts as a nuclear localization signals (NLS), which results in the transport of the rev protein into the nucleus during viral replication. The rev protein is important for the synthesis of major viral proteins and is hence essential for viral replication.

In addition, the HIV genome contains a number of accessory regulatory proteins that generally are considered non-essential to the virus. Accessory regulatory proteins include the lentivirus protein R (vpr), the negative factor (nef) protein, the viral infectivity factor (vif), and the virus protein U (vpu). The vpr protein is a virion-associated, nucleocytoplasmic shuttling regulatory protein. It is believed to play an important role in replication of the virus, specifically, nuclear import of the pre-integration complex. The vpr protein also appears to cause its host cells to arrest their cell cycle in the G2 phase, which activates the host DNA repair machinery to enable integration of the viral DNA. In addition, the nef protein is a N-terminal myristoylated membrane-associated phosphoprotein involved in multiple functions during the replication cycle of the virus including, for example, apoptosis and increasing virus infectivity. The vif protein is a highly conserved, 23 kDa phosphoprotein important for the infectivity of HIV-1 virions depending on the cell type, and the vpu protein is a class I oligomeric integral membrane phosphoprotein with numerous biological functions.

As indicated herein, an unnatural amino acid (UAA*)-mediated blank codon suppression system (FIG. 1) has been developed and used to prevent the proper translation and assembly of viable virus particles by introducing at least one (e.g., one or more; e.g., at least two, at least three) UAA*-mediated blank codons into one or more essential regions of the HIV virus. It would be appreciated by a skilled artisan that UAA*-mediated blank codons also can be referred to as "nonsense mutations." As used herein, a "nonsense mutation" refers to a mutation that produces a codon (e.g., an amber codon, an ochre codon, an opal or umber codon) that does not encode a natural proteinogenic amino acid. As described herein, however, the system allows for assembly of live and functional HIV particles in the presence of a corresponding tRNA, referred to herein as a "suppressor tRNA." For the suppressor tRNA to be present and capable of decoding the blank codon, the system further requires the corresponding aminoacyl-tRNA synthetase (aaRS). It would be understood that the corresponding suppressor tRNA and aminoacyl-tRNA synthetase oftentimes are referred to as a "pair."

Two systems, *E coli* $tRNA^{Tyr}$-tyrosyl-tRNA synthetase (TyrRS) pair and archaeal $tRNA^{Pyl}$-pyrrolysyl-tRNA synthetase (PylRS) pair, have been developed to decode either nonsense (Liu et al., 2007, Nat. Methods, 4:239-44; Chen et al., 2009, Angew. Chem. Int. Ed., 48:4052-5; Wang et al. 2007, Nat. Neurosci., 10:1063-72) or frameshift (Niu et al., 2013, ACS Chem. Biol., 8:1640-5) codons in mammalian cells. However, the complicated assembly process of human viruses has made it very challenging to genetically incorporate mutations, and particularly nonsense mutations, into the proteins of live human viruses using either of the above two systems. This disclosure, however, has accomplished that feat.

Specifically, as described herein, a $tRNA^{Tyr}$-4-azidophenylalanyl-tRNA synthetase (AzFRS) pair, a $tRNA^{Tyr}$-4-acetylphenylalanyl-tRNA synthetase (AcFRS) pair, and a $tRNA^{Tyr}$-4-iodophenylalanyl-tRNA synthetase (IodoFRS) pair (see, for example, Liu et al., 2007, Nat. Methods, 4:239-44) were used. All three amino acids have similar sizes to that of tyrosine, and the AzF and AcF molecules (FIG. 2A) also contain unique functional groups that allow selective modification of viral proteins through bioorthogonal reactions. The methods and systems described herein, however, are not limited to either an *E coli* $tRNA^{Tyr}$-tyrosyl-tRNA synthetase (TyrRS) pair or an archaeal $tRNA^{Pyl}$-pyrrolysyl-tRNA synthetase (PylRS) pair; the methods and systems described herein are amenable to virtually any suppressor tRNA-aminoacyl-tRNA synthetase pair that are identified or designed.

The HIV genome can be engineered to contain multiple and different mutations within one or more essential regions, which further attenuates and controls the virus. For example, a second mutation can be a mutation that encodes for a second unnatural amino acid (UAA*) within the same or a different essential region. In some embodiments, a second or further mutation can encode, for example, a photoreactive amino acid. Photoreactive amino acids are known in the art and include, for example, photocaged amino acids (e.g., ONBK, ONBY) that, upon exposure to light of a particular wavelength, revert to the natural amino acid.

A mutation as described herein can be the result of a point mutation, an insertion, a deletion, a substitution, or combinations thereof. Introducing a mutation into a sequence is known in the art, and one or more mutations can be introduced into a viral genome using routine methods such as, without limitation, PCR-mediated mutagenesis or other recombinant nucleic acid techniques (e.g., restriction enzyme digestion, chemical synthesis, ligation, and combinations thereof).

To suppress a mutation as described herein (e.g., a nonsense mutation), the suppressor tRNA-aminoacyl-tRNA synthetase pair can be provided on at least one transgene, operably linked to one or more expression elements. Expression elements include nucleic acid sequences that direct and regulate expression of coding sequences. One example of an expression element is a promoter sequence. Expression elements also can include introns, enhancer sequences, response elements, or inducible elements that modulate expression of a nucleic acid. Expression elements can be of viral origin or bacterial, yeast, insect, or mammalian origin, and transgenes or vectors containing one or more transgenes can contain a combination of expression elements from different origins.

It would be appreciated by a skilled artisan that the one or more transgenes encoding a suppressor tRNA and the corresponding aminoacyl-tRNA synthetase can be contained within one or more vectors. Vectors, including expression vectors, are commercially available or can be produced by recombinant DNA techniques routine in the art. A vector containing a nucleic acid can have expression elements operably linked to such a nucleic acid, and further can include sequences such as those encoding a selectable marker (e.g., an antibiotic resistance gene). As used herein, operably linked means that a promoter or other expression element(s) are positioned relative to a coding sequence so as to direct or regulate expression of the nucleic acid (e.g., in-frame).

One or more vectors containing at least one transgene (i.e., encoding a suppressor tRNA and corresponding aminoacyl-tRNA synthetase pair) can be introduced into a host cell. As used herein, "host cell" refers to the particular cell into which the nucleic acid is introduced and also includes the progeny of such a cell that carry the vector. A host cell can be a prokaryotic or eukaryotic cell. For example, a transgene as described herein can be expressed in bacterial cells such as *E. coli*, or in yeast, plant cells, or mammalian cells (e.g., human 293T cells). Other suitable host cells are known to those skilled in the art. Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer. In some cases, the choice of methods will depend upon whether integration into the genome of the host cells is desired or required, or whether transient expression or extrachromosomal expression from a vector (e.g., a replicating plasmid) is desired.

Alternatively, and as discussed herein, the at least one transgene (e.g., at least two transgenes, at least three transgenes) encoding the suppressor tRNA and corresponding aminoacyl-tRNA synthetase pair can be introduced into the HIV genome. In this embodiment, the at least one transgene is introduced into a non-essential region of the HIV genome that allows transcription and translation and does not interfere with replication and packaging. It would be appreciated that, from a safety perspective, expression of the suppressor tRNA and corresponding aminoacyl-tRNA synthetase pair from the HIV genome requires that the nonsense mutation encodes for an amino acid that does not exist in the host and, preferably, does not exist in nature.

Methods of maintaining a live, attenuated HIV vaccine are known in the art, and typically include infecting a host cell with the live, attenuated HIV vaccine. The host cell, under these circumstances, typically is determined by the virus' host specificity. As discussed herein, if the viral genome does not contain a transgene encoding the suppressor tRNA and corresponding aminoacyl-tRNA synthetase pair, then the at least one transgene encoding the suppressor tRNA and corresponding aminoacyl-tRNA synthetase pair needs to be provided by the host cell in order to suppress the mutation. In addition, if any of the mutations include a photoreactive amino acid, then the appropriate light needs to be provided in order to suppress the mutation. Following infection, the live, attenuated HIV vaccine described herein can be purified. As used herein, purifying a live, attenuated HIV vaccine refers to a process that removes the vaccine from the host cell or from the culture in which the host cell is growing.

In addition, an article of manufacture if provided for producing or maintaining a live, attenuated HIV vaccine. An article of manufacture as described herein can include a live, attenuated HIV vaccine as described herein, and at least one unnatural amino acid (UAA*). An article of manufacture also can include an appropriate host cell, which, if necessary, includes the at least one transgene encoding the suppressor tRNA and the corresponding aminoacyl-tRNA synthetase pair that recognizes the unnatural amino acid. In some embodiments, an article of manufacture can include one or more (e.g., two or more, three or more) photoreactive amino acids and, if necessary, at least one transgene encoding the suppressor tRNA and the corresponding aminoacyl-tRNA synthetase pair that recognizes the photoreactive amino acid.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1

General

All chemicals and DNA oligomers were obtained from commercial sources and used without further purification.

Unnatural amino acids (UAA*s), 4-azidophenylalanine (AzF) and 4-iodophenylalanine (IodoF), were purchased from Bachem. The synthesis of 4-acetylphenylalanine (AcF)

follows the procedure that was previously reported (Wang et al., 2003, PNAS USA, 100:56-61).

HIV-1 clone, pSUMA.c/2821, Cat#11748, referred to herein as "pSUMA", is an infectious molecular clone of a founder/transmitter HIV-1 virus and was obtained through the NIH AIDS Reagent Program, Division of AIDS, NIAID, NIH, from Dr. John Kappes and Dr. Christina Ochsenbauer.

E. coli DH10B and GeneHogs were used for routine cloning and DNA propagation. E. coli Stb1-2 (Life Technologies) was use for pSUMA manipulations.

Standard molecular biology techniques (Sambrook et al., 2000, Molecular Cloning: A Laboratory Manual, Third Ed., Cold Spring Harbor Laboratory Press) were used throughout.

Example 2

Plasmid Construction pcDNA3.1-tRNA$^{Tyr}$: The suppressor tRNA$^{Tyr}$ was derived from E. coli. The G35 of the tRNA$^{Tyr}$ was mutated to C to generate CUA anticodon. The tRNA$^{Tyr}$ gene lacking 3'-CCA but with a 3'-TTTTTCT sequence was PCR amplified. A human U6 promoter was PCR amplified from pCMV-pylRSNBK-1 (Chen et al., 2009, Angew. Chem. Int. Ed., 48:4052-5 and 121:4112-5) and added in front of the tRNA$^{Tyr}$ gene by overlapping PCR. The U6-tRNA$^{Tyr}$ gene cassette was PCR amplified and inserted into pcDNA3.1/hygro(+) (Life Technologies) in front of the CMV promoter to afford pcDNA3.1-tRNA$^{Tyr}$.

pAzFRS: The AzFRS-encoding gene was PCR amplified from plasmid pSWAN-pAzpaRS (Liu et al., 2007, Nat. Methods 4:239-44) and inserted into pcDNA3.1-tRNA$^{Tyr}$ behind the non-regulated CMV promoter to afford plasmid pAzFRS.

pAcFRS: The AcFRS-encoding gene was PCR amplified from plasmid pSWAN-pApaRS (Liu et al., 2007, Nat. Methods 4:239-44) and inserted into pcDNA3.1-tRNA$^{Tyr}$ behind the non-regulated CMV promoter to afford plasmid pAcFRS.

pIodoFRS: The IodoFRS-encoding gene was PCR amplified from plasmid pSWAN-pIpaRS (Liu et al., 2007, Nat. Methods 4:239-44) and inserted into pcDNA3.1-tRNA$^{Tyr}$ behind the non-regulated CMV promoter to afford plasmid pIodoFRS.

pEGFP-TAG40: The EGFP-encoding gene containing an amber stop codon (UAG) at a permissive site (Tyr40) was inserted into pcDNA3.1-tRNA$^{Tyr}$ behind the non-regulated CMV promoter to afford plasmid pEGFP-TAG40.

pSUMA Mutants: Overlapping PCR was used to introduce amber mutations onto the HIV-1 genome that is encoded by plasmid pSUMA. The following primers were used to introduce amber mutations:

pSUMA-Tyr132

(SEQ ID NO: 1)
5'-CTAGAACGATTCGCAGTTAACCCTG-3'

(SEQ ID NO: 2)
5'-GTTCTGCACTATAGGCTAATTTTGGCTGACCTGGCTG-3'

(SEQ ID NO: 3)
5'-TAGCCTATAGTGCAGAACCTCCAG-3'

(SEQ ID NO: 4)
5'-GTGCCTATAGCTTTGTGTCCACAG-3' pSUMA-Ala119

(SEQ ID NO: 5)
5'-CTAGAACGATTCGCAGTTAACCCTG-3'

(SEQ ID NO: 6)
5'-TTTCCTGCGTCAGCctaTGCTTGCTGTGCTTTTTTCTTAC-3'

(SEQ ID NO: 7)
5'-CTGACGCAGGAAACAACAGCCAG-3'

(SEQ ID NO: 8)
5'-GTGCCTATAGCTTTGTGTCCACAG-3' pSUMA-Leu365

(SEQ ID NO: 9)
5'-CAAAGTAAGACAATATGATCAGGTAAC-3'

(SEQ ID NO: 10)
5'-CACCTCTACAGATGTTCTCTCAGTTCCTC-3'

(SEQ ID NO: 11)
5'-CATCTGTAGAGGTGGGATTTACCACAC-3'

(SEQ ID NO: 12)
5'-GCTTCCCATGTTTCTCTTTGTATG-3' pSUMA-Tyr59

(SEQ ID NO: 13)
5'-CTAGAACGATTCGCAGTTAACCCTG-3'

(SEQ ID NO: 14)
5'-ATTTCTATGGTTACCTGATCCTATTGTCTTACTTTGATAAAAC-3' pSUMA-Trp36Gln127

(SEQ ID NO: 15)
5'-GTAGAGGATCCACTAGTAAC-3'

(SEQ ID NO: 16)
5'-TAGCTCCCTGCTTGCCTATACTATATGTTTTAATTG-3'

(SEQ ID NO: 17)
5'-GGCAAGCAGGGAGCTAGAAC-3'

(SEQ ID NO: 18)
5'-GTGCCTATAGCTTTGTGTCCACAG-3' pNL-GI-Tyr40: Overlapping PCR was used to introduce amber mutations onto the GFP gene that is encoded on plasmid pNL-GI (Collins et al., 1998, Nature, 391:397-401). The following primers are used to introduce the amber mutation:

(SEQ ID NO: 19)
5'-GCTATAAGACGCGTCCACCATG-3'

(SEQ ID NO: 20)
5'-CCTAGGTGGCATCGCCCTC-3'

(SEQ ID NO: 21)
5'-CGATGCCACCTAGGGAAAGCTGACCCTGAAGTTC-3'

(SEQ ID NO: 22)
5'-CGTCTAGATTACTTGTACAGCTCATC-3'

Example 3

Protein Expression and Purification 293T cells were grown in media containing DMEM, 10% FBS (v/v), and 2 mM L-glutamine at 37° C. in a humidified atmosphere of 5% $CO_2$ (v/v). When cells reached 60-70% confluency, they were transfected with plasmids pEGFP-40TAG and pAzFRS using Lipofectamine™ 2000 (Life Technologies) according to the manufacturer's protocol (36 µL Lipofectamine 2000+12 µg of pAzFRS+12 µg of pEGFP-TAG40 for 12 mL cell culture in 75 cm$^2$ cell-culture flask).

Six hours posttransfection, the culture medium was carefully removed and replaced with 12 ml of fresh medium containing 1 mM AzF. Cells were grown for an additional 36 h before being washed with DPBS, lysed with RIPA buffer (Thermo Scientific), and partially purified using Ni-NTA resin (GE Healthcare) according to the manufacturer's protocol.

Example 4

Transfection and Generation of Live HIV-1

293T cells were grown in a medium containing DMEM, 10% FBS, and 2 mM L-glutamine at 37° C. in a humidified atmosphere of 5% $CO_2$. When cells reached 60-70% confluency, they were transfected with appropriate plasmid(s) using Lipofectamine 2000 (10 μl Lipofectamine 2000+3 μg of plasmid(s) for 2 ml cell culture in a 6-well plate) by following standard procedures provided by the manufacture (Life Technologies). Six hours posttransfection, the culture medium was carefully removed and replaced with 2 ml of fresh medium. When it was needed, UAA* was added to a final concentration of 1 mM. After 44-48 hours of incubation, virus-containing culture supernatant was harvested by collecting the medium from the well using a pipette. The FBS concentration in the virus-containing culture medium was then adjusted to 20% (i.e. for each 1 ml of harvested virus, 0.125 ml of FBS was added). The virus-containing culture medium was then filtered through a 0.45-micron filter. The virus was used directly or aliquoted into sterile screw-cap vials and stored at −80° C.

Example 5 p24 Assay

P24 assay was measured with Retrotek HIV-1 p24 Antigen ELISA 2.0 by following standard procedures provided by the manufacture (ZeptoMetrix Corporation). Briefly, 200 μl cell culture samples, the standard, and the control were added to the monoclonal antibody-coated micro-plate wells and incubated at 37° C. for 1.5 hour. After washing and the addition of antibody-HRP conjugate, the micro-plate was incubated at 37° C. for one hour. Plates were then washed and the HRP-substrate was added for color development. The reactions were stopped by the addition of 1 M $H_2SO_4$2504 and absorbance values were determined at 450 nm. The amount of p24 is determined by interpolation from a point-to-point plot or from a linear regression analysis of the standard curve.

Example 6

Infection Assay

HIV-1 infection was quantified with X-gal staining based assay with TZM-bl cells. Briefly, virus (generated in the presence of UAA*), 50 μl 10% DMEM growth medium, and DEAE-dextran at a final concentration of 40 mg/ml were added to each well (96-well flat bottom plate) that contains TZM-bl cells ($1\times10^4$ per well in 100 μl volume) in triplicate. Assay controls included: (1) replicate wells of TZM-bl cells with virus that are generated in the absence of UAA*; (2) growth medium only control; and (3) TZM-bl cell only control. After 48-hour incubation at 37° C., 200 μl of assay medium was removed from each well. Plates were then washed, fixed, and stained using X-gal solution followed by examination using a light microscope.

Example 7

Tissue Culture Infectious Dose 50 (TCID50)

Infectious titers of all viruses were determined by standard Tissue Culture Infectious Dose 50 (TCID50) method with X-gal staining assay (see above) in TZM-bl cells. Briefly, four-fold serial dilutions of virus were performed in quadruplicate (96-well flat bottom plate) in the X-gal staining assay. The TCID50 of the virus was calculated by Spearman-Karber formula according to the negative end-point and dilution folds.

Example 8

Fluorescence Spectroscopy and Cell Imaging

The fluorescent images and bright-filed images were taken by a Nikon ECLIPSE TE3000 microscope and an EVOS FL Auto Imaging System with DIC. The cells were excited at 488 nm to acquire EGFP fluorescence images at 530/25 nm.

Example 9

LC/MS/MS Assays

The corresponding protein band of EGFP-40TAG from SDS-PAGE was cut and in-gel digested with trypsin (in 50 mM ammonium bicarbonate, pH 8.0) overnight at 37° C. The resulting peptide fragments were extracted with 0.1% formic acid/75% acetonitrile, and then subjected to LC/MS/MS analysis using a Waters Q-TOF Ultima. Database searches were performed on an in-house Mascot server (Matrix Science Ltd., London, UK). For AzF substitution site mapping on EGFP, AzF substitution for tyrosine was included as a variable modification.

Example 10

Suppression Efficiency and Fidelity

Figure 2:
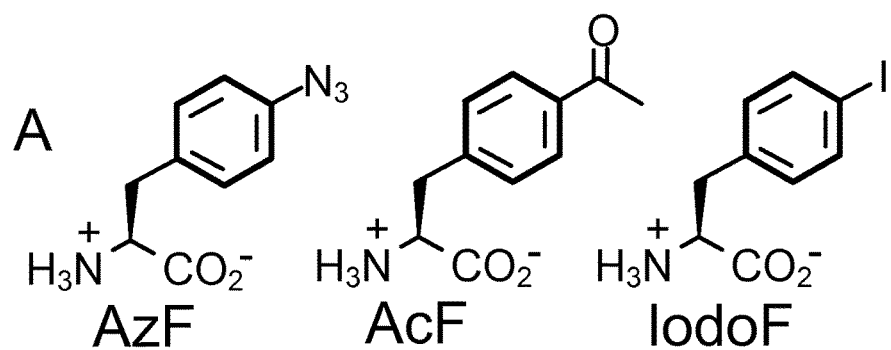
FIG. 2 is data showing controlled EGFP expression in 293T cells. Panel (A) is the chemical structures of 4-azidophenylalanine (AzF); 4-acetylphenylalanine (AcF), and 4-iodophenylalanine (IodoF); Panel (B) is a schematic showing EGFP with an Amber codon at position 40; Panel (C) demonstrates EGFP expression in the presence of the tRNA$^{Tyr}$-AzFRS pair and 1 mM of AzF; Panel (D) demonstrates EGFP expression in the presence of the tRNA$^{Tyr}$-AzFRS pair, but without AzF. Scale bars, 200 μm.
Figure 2:
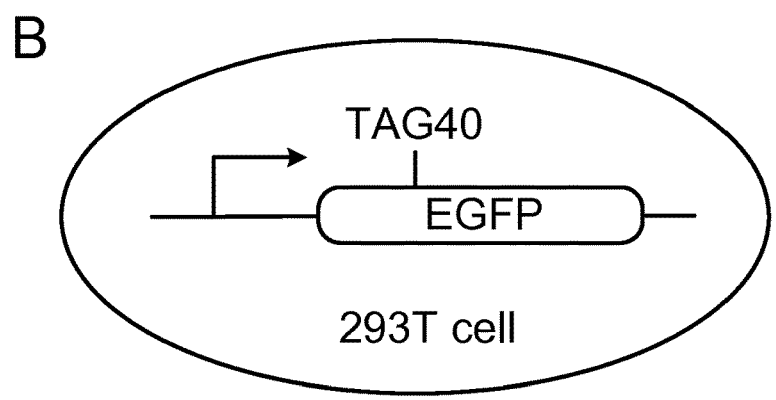
Figure 2:
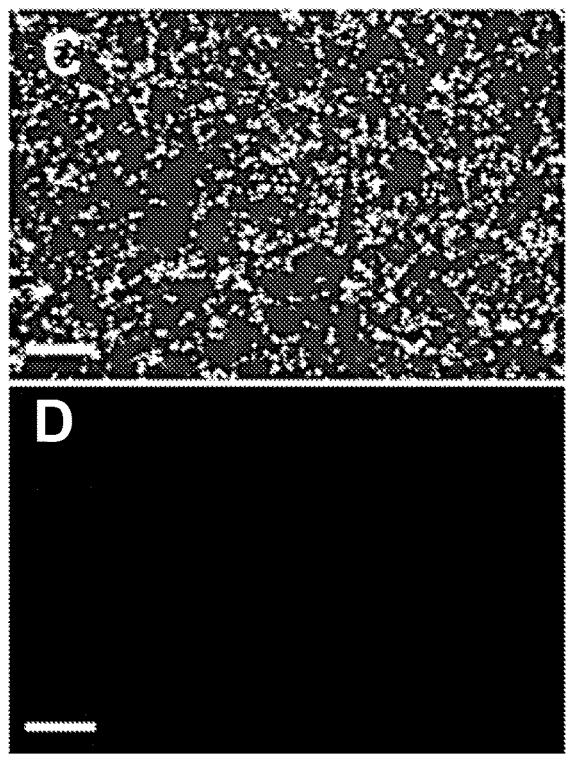
Figure 9:
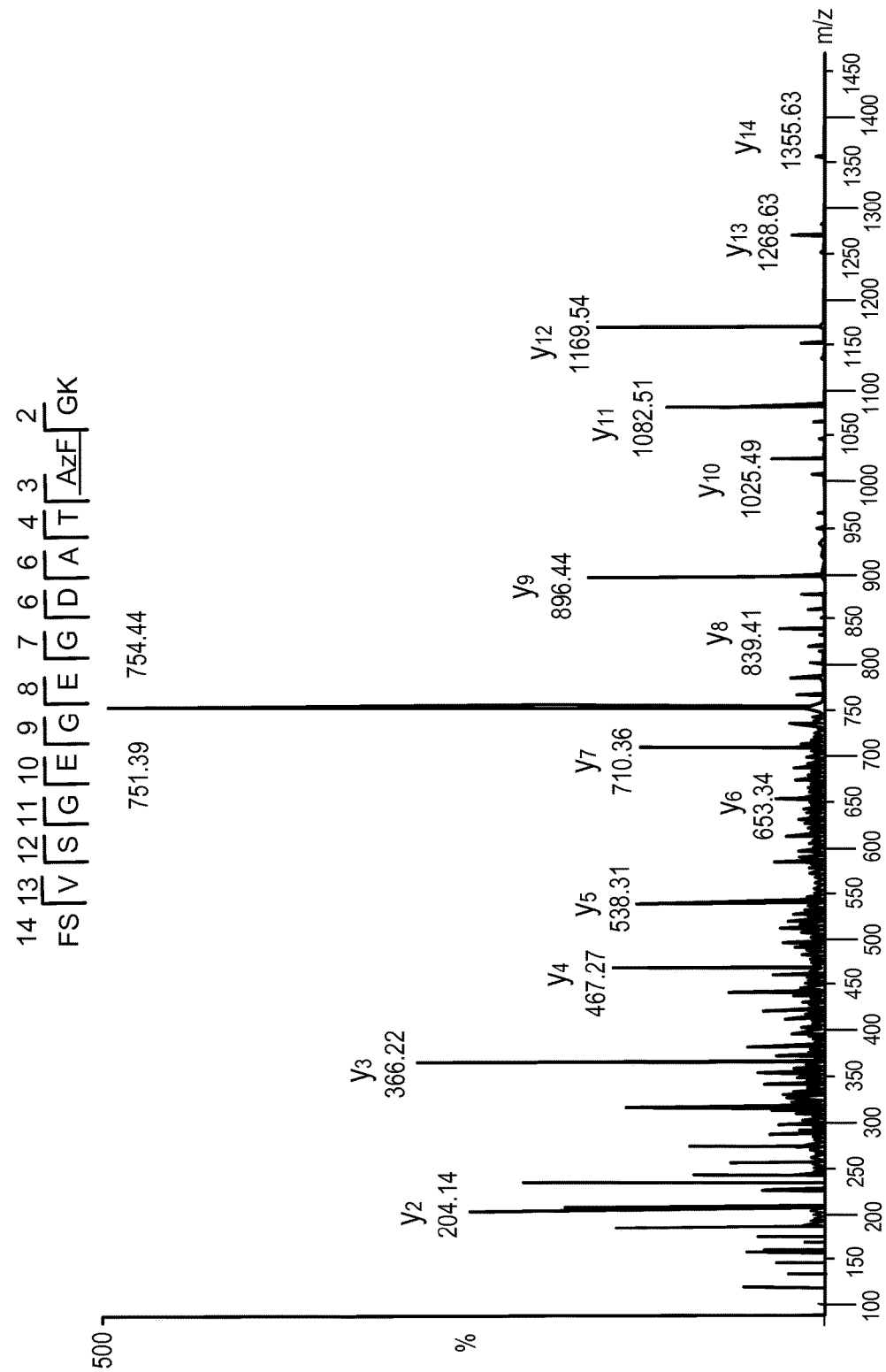
FIG. 9 shows mass spectrometry analysis of EGFP containing AzF at position 40. The y ions are marked in the spectrum. The amino acid sequence of the peptide fragment, FSVSGEGEGDATAzFGK (SEQ ID NO:23), from mutant EGFP containing AzF is shown on top. The amber mutation site contained exclusively 4-aminophenylalanine (aminoF), which is the reduction product of AzF. This observation is consistent with previous reports on the mass spectrometry analyses of AzF-containing proteins.
Figure 10:
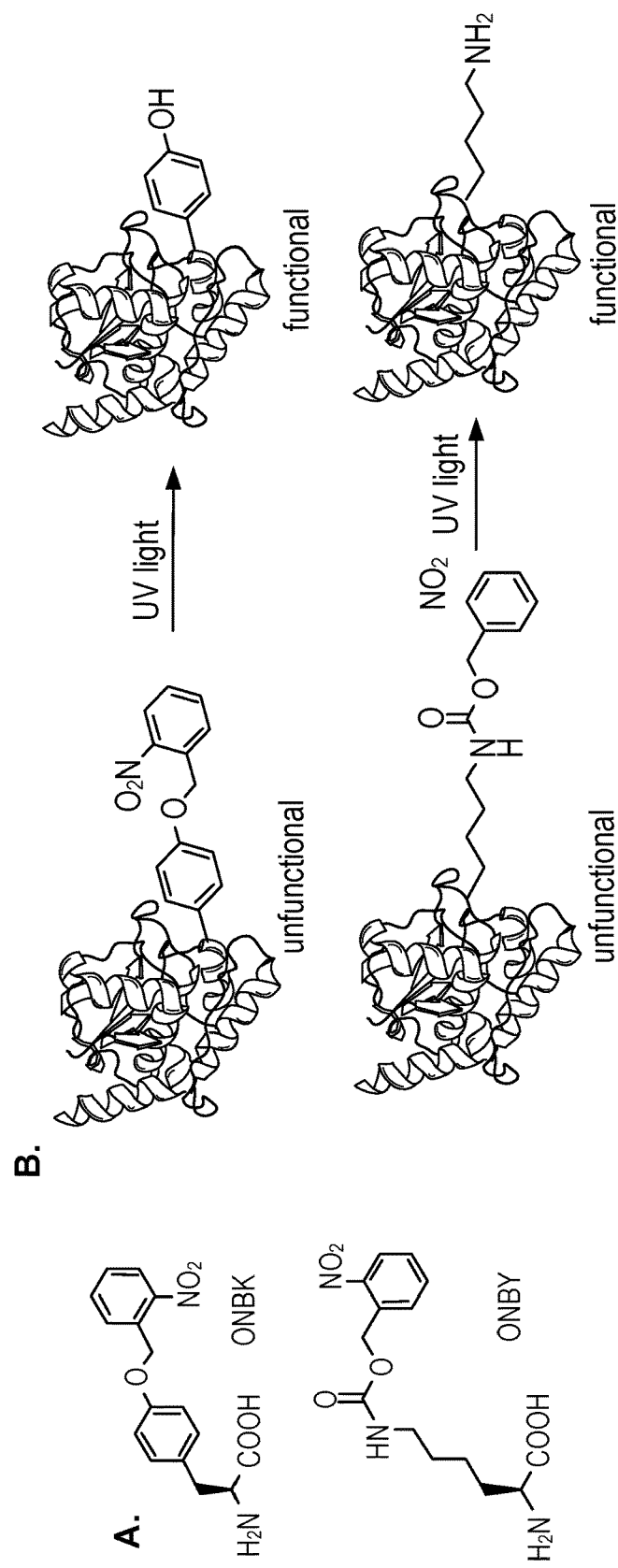
FIG. 10 is a schematic showing photo-regulation of protein function. Panel (A) shows the structures of ONBY and ONBK; Panel (B) shows the restoration of protein function with UV light.
Figure 11:
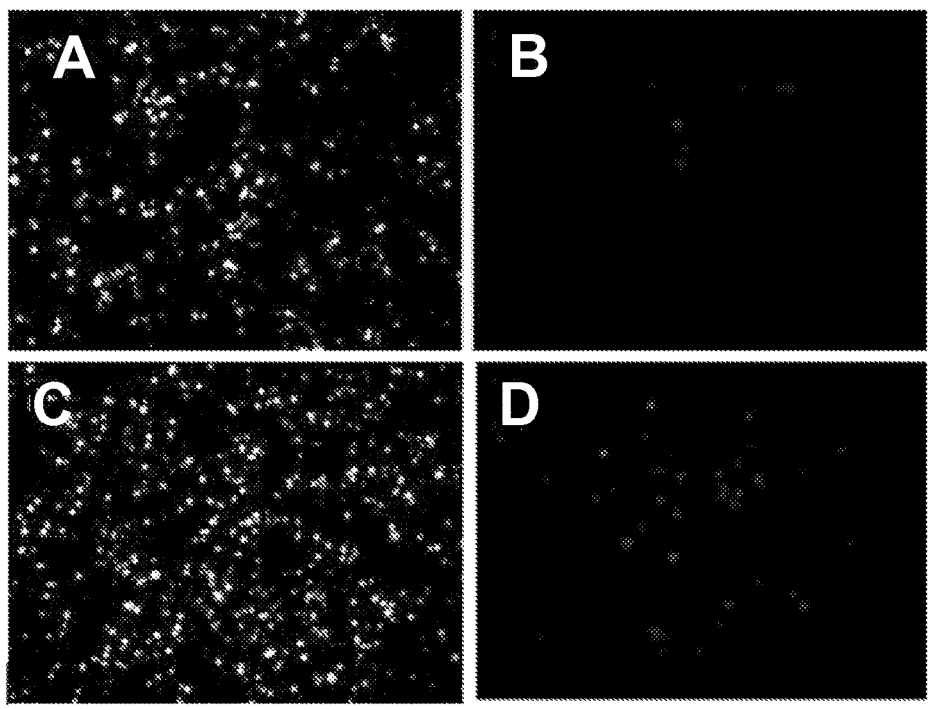
FIG. 11 is data demonstrating the incorporation of ONBY and ONBK into EGFP-Y40 in 293T cells. Panel (A) shows 293T cells containing pEGFP-Y39TAG and pcDNA-U6-PylT-ONBY in the presence of 0.4 mM ONBY; Panel (B) shows 293T cells containing pEGFP-Y39TAG and pcDNA-U6-PylT-ONBY in the absence of 0.4 mM ONBY; Panel (C) shows 293T cells containing pEGFP-Y39TAG and pCMV-ONBK in the presence of 1 mM ONBK; Panel (D) shows 293T cells containing pEGFP-Y39TAG and pCMV-ONBK in the absence of 1 mM ONBK.
Figure 12:
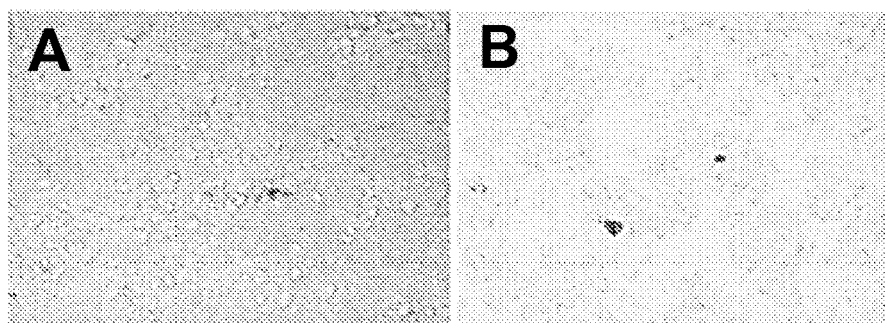
FIG. 12 is data demonstrating the infectivity of pSUMA-d1d2-AzFRS and pSUMA-d1d2-TyrRS. Panel (A) shows the infection of TZM-b1 cells with pSUMA-d1d2-AzFRS; Panel (B) shows the infection of TZM-b1 cells with pSUMA-d1d2-TyrRS.
Figure 13:
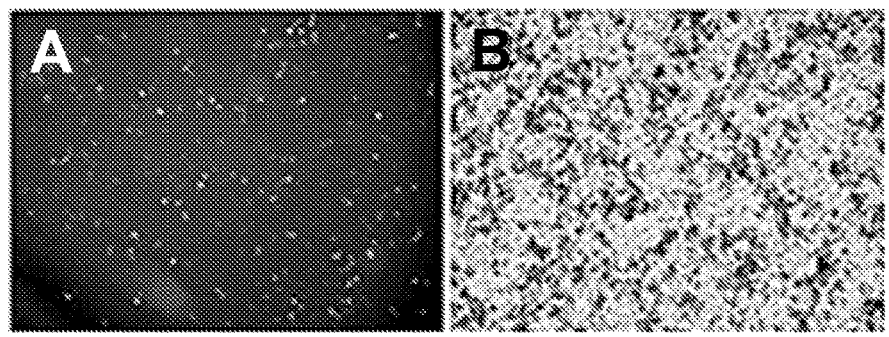
FIG. 13 is data demonstrating EGFP expression and infectivity of pSUMA-EGFP mutant. Panel (A) shows a fluorescence image of 293T cells containing pSUMA-EGFP; Panel (B) shows the infection of TZM-b1 cells with pSUMA-EGFP-derived HIV-1 mutant.

To examine the nonsense (e.g., amber) suppression efficiency and fidelity of the $tRNA^{Tyr}$-AzFRS pair, 293T cells were co-transfected with a plasmid containing $tRNA^{Tyr}$ under the control of a human U6 promoter and the AzFRS (pAzFRS) with a plasmid encoding EGFP with an amber mutation at residue 40 (pEGFP-TAG40). Following transfection, cells were cultured in DMEM media (containing 10% FBS and 2 mM L-glutamine) with or without 1 mM AzF for 12 h before visualization under a fluorescence microscope (FIGS. 2C and 2D). Full-length EGFP was detected only in cells supplemented with 1 mM AzF (FIG. 2C), while no EGFP was observed otherwise (FIG. 2D). The tandem mass spectrometry data (FIG. 9) showed no undesirable incorporation of tyrosine or any other natural amino acids. The amber mutation site contained exclusively 4-aminophenylalanine (aminoF), which is the reduction product of AzF. These results confirmed the excellent fidelity of AzF incorporation, and are consistent with previous reports on the mass spectrometry analyses of AzF-containing proteins.

Example 11

Suppression of the Gag Protein

Figure 3:
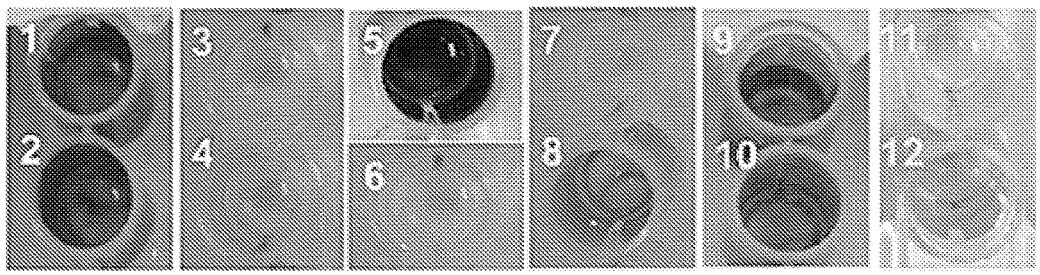
FIG. 3 is data demonstrating that HIV-1 replication can be controlled with Amber suppression. Panel (A) shows a p24 assay after transfection of 293T with pSUMA variants. The absorbance values were determined at 450 nm after the colorimetric reactions were stopped by the addition of 1 M $H_2SO_4$. Well #11 was used as a blank for all measurements. Well #1, wild-type pSUMA only; Well #2, wild-type pSUMA+tRNA$^{Tyr}$-AzFRS pair+1 mM AzF; Well #3, pSUMA-Tyr132+tRNA$^{Tyr}$-AzFRS pair, without AzF; Well #4, pSUMA-Tyr132+tRNA$^{Tyr}$-AzFRS pair, with 1 mM AzF; Well #5, pSUMA-Tyr132+tRNA$^{Tyr}$-TyrRS pair; Well #6, pSUMA-Tyr132; Well #7, pSUMA-Ala119+tRNA$^{Tyr}$-AzFRS pair, without AzF; Well #8, pSUMA-Ala119+tRNA$^{Tyr}$-AzFRS pair, with 1 mM AzF; Well #9, pSUMA-Leu365+tRNA$^{Tyr}$-AzFRS pair, without AzF; Well #10, pSUMA-Leu365+tRNA$^{Tyr}$-AzFRS pair, with 1 mM AzF; Well #11, negative ELISA control, no p24; Well #12, positive ELISA control, 125 pg/ml p24; Panels (B)-(I) are data from infection assays with TZM-b1 cells. Panel (B) shows cells infected with virus collected from the sample described in Well #1; Panel (C) shows cells infected with virus collected from the sample described in Well #2; Panel (D) shows cells infected with virus collected from the sample described in Well #4; Panel (E) shows cells infected with virus collected from the sample described in Well #3; Panel (F) shows cells infected with virus collected from the sample described in Well #5; Panel (G) shows cells infected with virus collected from the sample described in Well #6; Panel (H) shows cells infected with virus collected from the sample described in Well #8; Panel (I) shows cells infected with virus collected from the sample described in Well #10. Scale bars, 100 μm.
Figure 3:
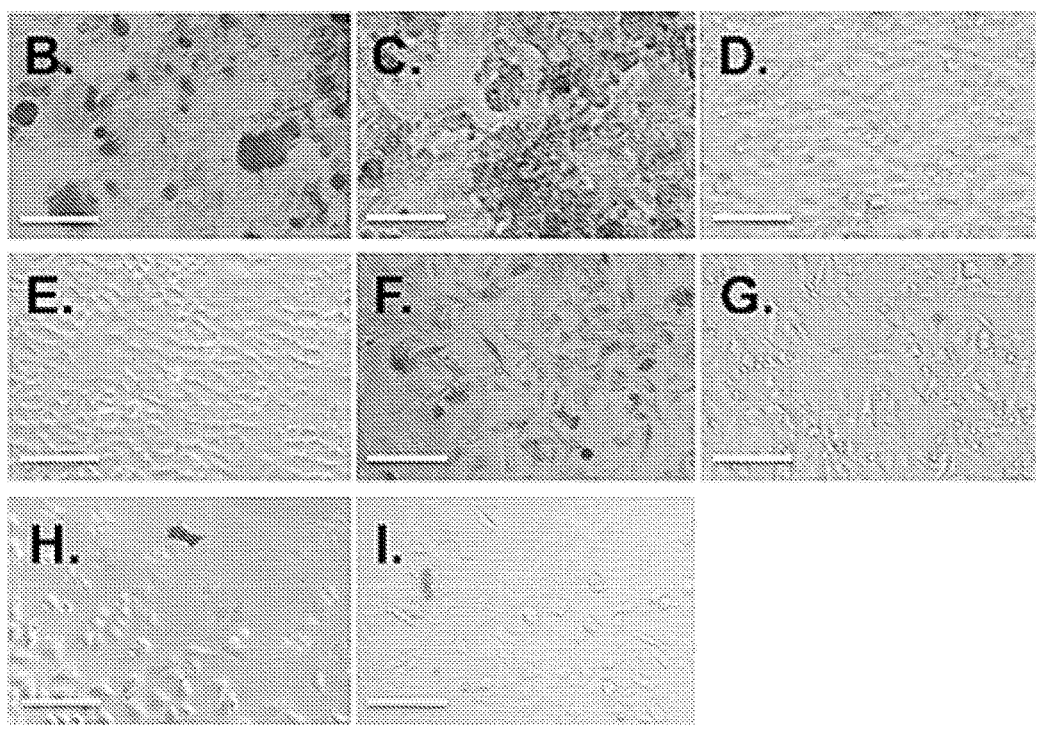
Figure 6:
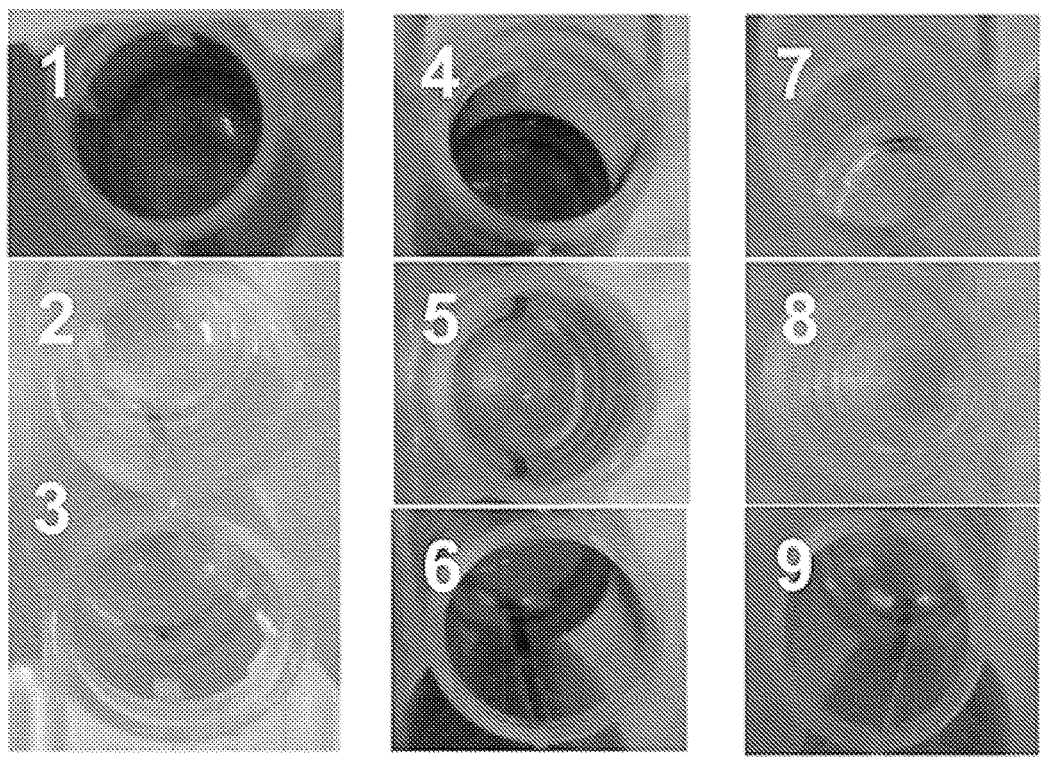
FIG. 6 is data showing p24 assays after transfection of 293T with pSUMA variants. Well #1, wild-type pSUMA control; Well #2, negative ELISA control, no p24; Well #3, positive ELISA control, 125 pg/ml p24; Well #4, pSUMA-Tyr132+tRNA$^{Tyr}$-AcFRS pair, with 1 mM AcF; Well #5, pSUMA-Ala119+tRNA$^{Tyr}$-AcFRS pair, with 1 mM AcF; Well #6, pSUMA-Leu365+tRNA$^{Tyr}$-AcFRS pair, with 1 mM AcF; Well #7, pSUMA-Tyr132+tRNA$^{Tyr}$-IodoFRS pair, with 1 mM IodoF; Well #8, pSUMA-Ala119+tRNA$^{Tyr}$-IodoFRS pair, with 1 mM IodoF; Well #9, pSUMA-Leu365+tRNA$^{Tyr}$-IodoFRS pair, with 1 mM IodoF. Well #2 was used as a blank for p24 assays.
Figure 7:
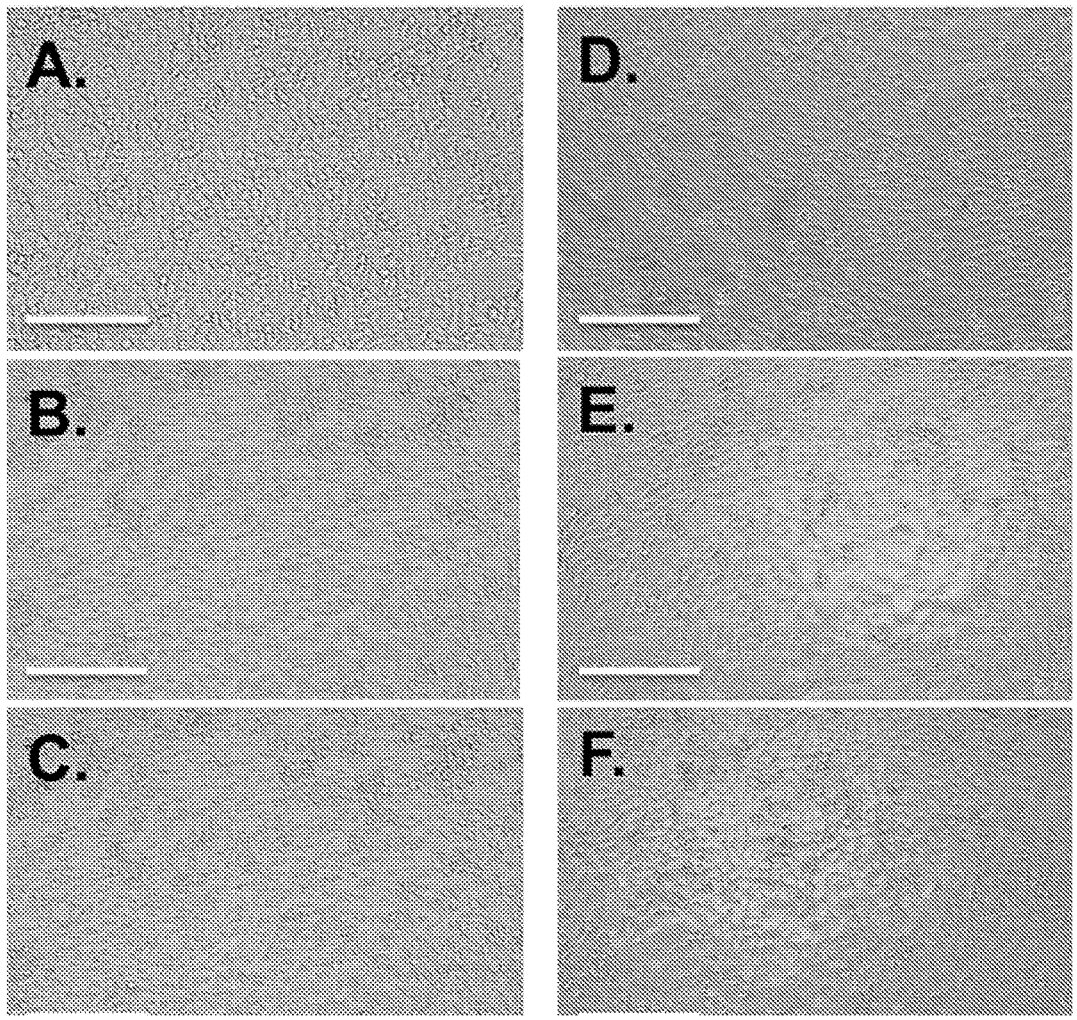
FIG. 7 shows infection assays with TZM-b1 cells using tRNA$^{Tyr}$-AcFRS pair and tRNA$^{Tyr}$-IodoFRS pair. Panel (A) shows cells infected with virus collected from pSUMA-Tyr132+tRNA$^{Tyr}$-AcFRS pair+1 mM AcF; Panel (B) shows cells infected with virus collected from pSUMA-Ala119+tRNA$^{Tyr}$-AcFRS pair+1 mM AcF; Panel (C) shows cells infected with virus collected from pSUMA-Leu365+tRNA$^{Tyr}$-AcFRS pair+1 mM AcF; Panel (D) shows cells infected with virus collected from pSUMA-Tyr132+tRNA$^{Tyr}$-IodoFRS pair+1 mM IodoF; Panel (E) shows cells infected with virus collected from pSUMA-Ala119+tRNA$^{Tyr}$-IodoFRS pair+1 mM IodoF; (F) infected with virus collected from pSUMA-Leu365+tRNA$^{Tyr}$-IodoFRS pair+1 mM IodoF. Scale bars, 200 μm.

The suppression of an amber codon in the HIV-1 genome was examined next. The Tyr132 codon on the Gag (group-specific antigen) protein-encoding gene was first mutated into an amber codon. The resulting pSUMA-Tyr132 was co-transfected into 293T cells with plasmid pAzFRS. After the cells were grown for 48 h in the presence or the absence of 1 mM AzF, viruses were harvested and the titer of HIV-1 was analyzed using anti-p24 antibody. The presence and the strength of a blue color suggest the presence and the level of the capsid protein p24. As shown in FIG. 3A (Wells #3 and #4), we observed an AzF-dependent p24 synthesis in pSUMA-Tyr132 mutant due to the essential role of Gag (Gag is processed during maturation to p24.) in p24 protein synthesis. The p24 assay confirmed a very high fidelity of AzF incorporation (absorbance values of 0.001 versus 0.453 in the absence and the presence of AzF, respectively; FIG. 3A, Wells #3 and #4). However, only very low level of p24 synthesis was observed comparing to that of the wild-type pSUMA control (FIG. 3A, Well #1). On the other hand, a very strong p24 synthesis was observed with the tRNA$^{Tyr}$-AcFRS pair (FIG. 6, Well #4) and an undetectable p24 synthesis was observed with the tRNA$^{Tyr}$-IodoFRS pair (FIG. 6, Well #7). Despite amber suppression and the synthesis of p24, little to no viral infection was observed when the harvested viruses were used to infect TZM-b1 cells (FIG. 3D and FIGS. 7A, 7D; The TZM-b1 cell line stably expresses large amounts of CD4 and CCR5 and should be highly sensitive to infections by diverse isolates of HIV-1. The TZM-b1 also contains a genome-copy of beta-galactosidase gene under the control of the HIV-1 promoter. The infection assay is based on the expression level of beta-galactosidase).

Figure 4:
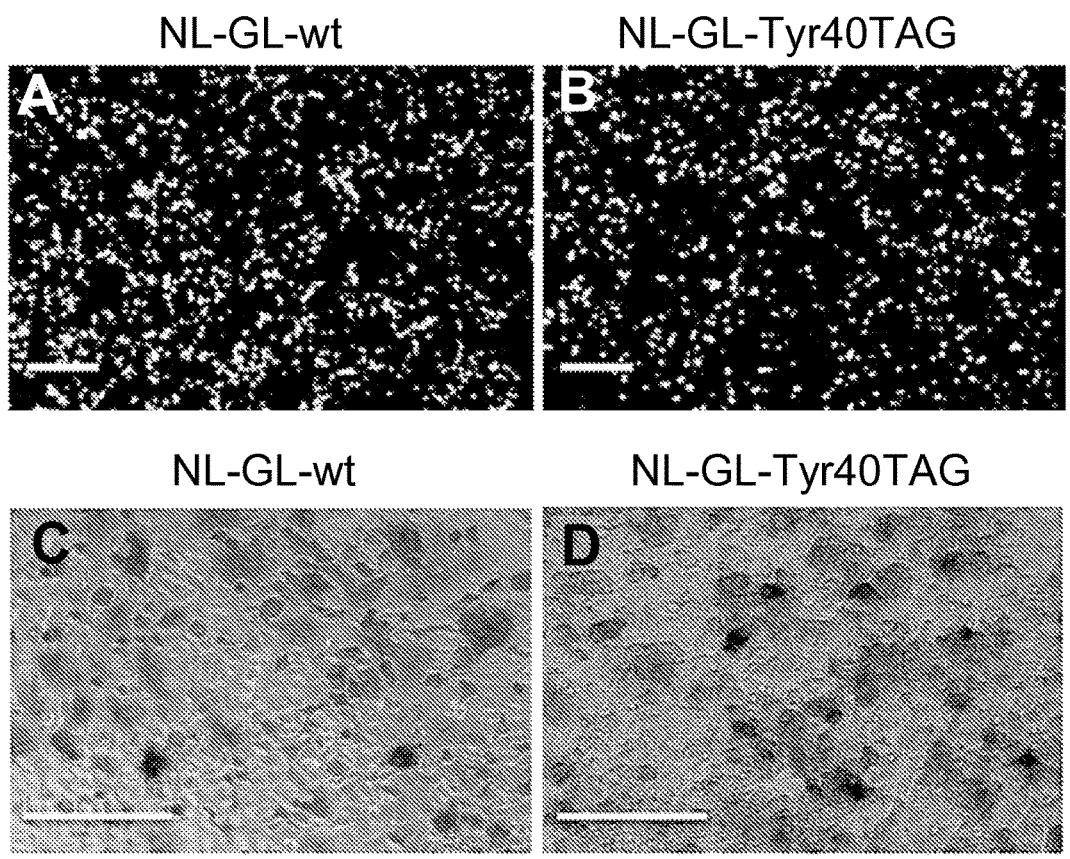
FIG. 4 is data showing expression and infection with pNL-GI variants. Panel (A) is a fluorescence image of pNL-GI; Panel (B) is a fluorescence image of pNL-GI-Tyr40+tRNA$^{Tyr}$-AzFRS pair, with 1 mM AzF; Panel (C) shows infection of TZM-b1cells with virus collected from the cells shown in FIG. 4, Panel (A); Panel (D) shows infection of TZM-b1 cells with virus collected from the cells shown in FIG. 4, Panel (B). Scale bars, 200 μm.

To explain the lack of live HIV-1 assembly from the above experiments, we first examined whether amber suppression can negatively affect HIV-1 protein syntheses, the virion assemble, and/or the infection since HIV-1 uses seven amber codons as stop signal. To this end, wild-type pSUMA was co-transfected with plasmid pAzFRS into 293T cells. After 48 h of cultivation in the presence of 1 mM AzF, viruses were harvested and the titer of HIV-1 was analyzed using anti-p24 antibody. We observed no obvious difference in p24 synthesis (FIG. 3A, Wells #1 and #2) and infection rate (FIGS. 3B and 3C) of wild-type pSUMA in the presence or the absence of the amber suppressing tRNA$^{Tyr}$-AzFRS pair. To further eliminate the possibility, we constructed a different HIV-1 mutant that was derived from pNL-GI (Collins et al., 1998, Nature, 391:964-7), which contains a copy of GFP inserted at the nef locus. In this new HIV-1 construct, an amber mutation was made at position 40 of GFP (originally encoding a tyrosine residue) and there was no amber mutation on the HIV-1 protein-encoding genes. The resulting HIV-1 variant, pNL-GI-Tyr40, was transfected into 293T cells together with plasmid pAzFRS. Strong GFP fluorescence (FIG. 4B) was detected when 1 mM of AzF was included in the culture medium. The fluorescence intensity is comparable to the wild-type pNL-GI (FIG. 4A), which indicated a very efficient amber suppression with the tRNA$^{Tyr}$-AzFRS pair. The produced HIV-1 viruses were then harvested and used to infect TZM-b1 cells. Near wild-type infection was observed (FIGS. 4C and 4D). Based on the above observations, we concluded that amber suppression did not have detectable detrimental effects on the viability of HIV-1.

It was then tested to see if UAA* incorporation at Tyr132 of Gag protein interfered with either the proper function or the post-translational processing of the Gag protein. To this end, the pSUMA-Tyr132 mutant was transfected into 293T cells with a plasmid containing tRNA$^{Tyr}$-TyrRS pair. The amber suppression led to the incorporation of a tyrosine residue at position 132, which produced the wild-type Gag protein. The p24 (FIG. 3A, Well #5) and infection (FIG. 3F) assays showed that the pSUMA-Tyr132 mutant, after amber suppression, had near wild-type activities. As a control, when pSUMA-Tyr132 was transfected into 293T cells that did not contain the tRNA$^{Tyr}$-TyrRS pair, no p24 synthesis was detected (FIG. 3A, Well #6) and no live viruses was assembled according to the infection assay (FIG. 3G). Combining these results and the results from UAA* incorporation, we concluded that incorporation of UAA* at position Tyr132 must have negative effect on the Gag protein expression and/or function.

Example 12

Suppression of the Gag or Pol Protein

Figure 8:
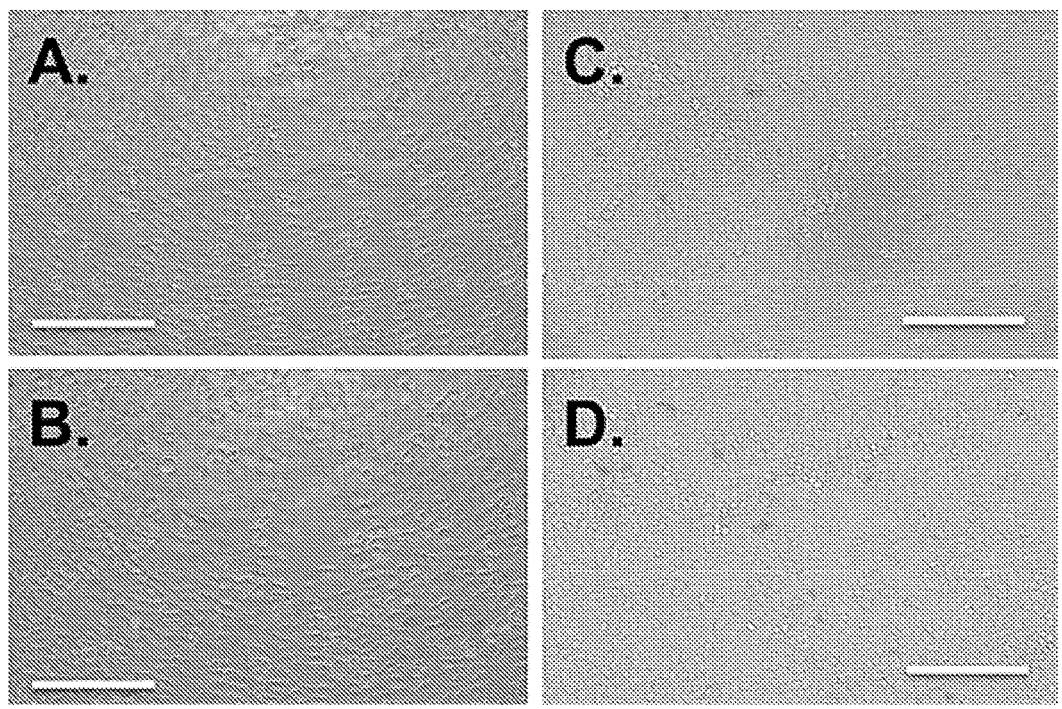
FIG. 8 shows infection assays with TZM-b1 cells using tRNA$^{Tyr}$-AzFRS pair. Panel (A) shows cells infected with virus collected from pSUMA-Ala119+tRNA$^{Tyr}$-AzFRS pair, without 1 mM AzF; Panel (B) shows cells infected with virus collected from pSUMA-Leu365+tRNA$^{Tyr}$-AzFRS pair, without 1 mM AzF; Panel (C) shows cells infected with pSUMA-Tyr59+tRNA$^{Tyr}$-AzFRS pair, without 1 mM AzF (the harvested viruses were concentrated 15 folds); Panel (D) shows cells infected with pSUMA-Trp36Gln127+tRNA$^{Tyr}$-AzFRS pair, without 1 mM AzF (the harvested viruses were concentrated 15 folds). Scale bars, 200 μm.

We next decided to examine other mutation sites and generated two new HIV-1 mutants, with amber mutation at Ala119 of Gag (pSUMA-Ala119) or Leu365 of Pol (pSUMA-Leu365). We initially focused on the amber suppression with the tRNA$^{Tyr}$-AzFRS pair in the presence of AzF. We observed an AzF-dependent p24 synthesis in pSUMA-Ala119 (FIG. 3A, Wells #7 and #8). The amber suppression at Ala119 position (FIG. 3A, Well #8) was apparently stronger than that at position Tyr132 of Gag (FIG. 3A, Well #4) and has similar good fidelity (absorbance values of 0.000 versus 2.127 in the absence and the presence of AzF, respectively; FIG. 3A, Wells #7 and #8). On the other hand, the synthesis of p24 in pSUMA-Leu365 was not AzF-dependent (FIG. 3A, Wells #9 and #10) since the amber mutation is in Pol, which does not affect p24 synthesis. Both mutants showed infection (FIGS. 3H and 3I) but with much lower activity than that of wild-type pSUMA (FIG. 3B). As a control, no infection was observed when AzF was not provided in the culture medium of 293T cells after transfection (FIGS. 8A, 8B). We next examined the tRNA$^{Tyr}$-AcFRS pair and tRNA$^{Tyr}$-IodoFRS pair. As shown in FIG. 6, a range from non-detectable to relative strong amber suppression was observed with the two tRNA-aaRS pairs and the different amber mutation sites (FIG. 6, Wells #5, #6, #8, and #9). However, no infection was detected when the tRNA$^{Tyr}$-AcFRS pair and tRNA$^{Tyr}$-IodoFRS pair were used to generate pSUMA-Ala119 and pSUMA-Leu365 mutants (FIGS. 7B, 7C, 7E, and 7F). Since the amber suppression efficiency did not correlate well with the infection results, we suspected that the structure of UAA*s and the incorporation sites might still partially interfere with the protein function.

Example 13

Suppression of the Protease Protein

An additional mutation site, Tyr59TAG (pSUMA-Tyr59) of HIV-1 protease was then examined. Since Tyr59 has similar structure to AzF and is away from the active site (PDB 1EBZ), mutation of which to AzF might not cause undesired disturbance of protein structure and function. Indeed, the pSUMA-Tyr59 mutant showed better infection activity (FIG. 5B) than that of the pSUMA-Ala119 (FIG.

3H) and pSUMA-Leu365 (FIG. 3I). As a control, no live pSUMA-Tyr59 virus was produced in the absence of AzF during viral assembly in 293T cells according to the infection assay (FIG. 8C). A comparison between the observed Tissue Culture Infectious Dose 50 (TCID50) values in the presence (1.31×103) and the absence of AzF (0.00) implicates high fidelity of the $tRNA^{Tyr}$-AzFRS pair.

The results above indicate that the UAA*-mediated suppression strategy can be used to produced live HIV-1 and the resulting virus is infectious. Since the infected cells do not contain the necessary suppression machinery (the special tRNA-aaRS pair and UAA*) that is required for HIV-1 assembly, no new virus can be assembled after the initial infection.

Example 14

All-In-One pSUMA Vector for In Vivo Experiments

In order to further examine the feasibility of controlling multiple cycles of HIV-1 replication with unnatural amino acid-mediated amber suppression, we needed to generate HIV-1 mutants that contain a genomic insertion of an amber suppressor tRNA and its corresponding aminoacyl-tRNA synthetase.

According to previous reports, the nef region of the HIV-1 genome tolerates deletions and/or insertions. We have obtained pSUMA-d1d2 constructs in which two regions of the nef gene were deleted. We examined the infectivity of pSUMA-d1d2 in humanized-BLT mice and demonstrated that pSUMA-d1d2 has near wild-type infectivity.

We next constructed pSUMA-d1d2-U6-tRNA by inserting U6-promoter-RNA-terminator cassette into the deleted nef region of HIV-1 genome. We also constructed pSUMA-d1d2-AzFRS and pSUMA-d1d2-TyrRS by inserting AzRS (for the incorporation of p-azido-phenylalanine) and TyrRS (for the incorporation of tyrosine), respectively, into the nef region of the HIV-1 genome. All three modified viruses showed weak infection. The results indicated that insertion into the nef region of genes of this size reduces the infectivity of virus.

Since gene insertion in the nef region is not well-tolerated, we next focused on a region between env and nef. A model viral genome, pSUMA-EGFP, was constructed by inserting an EGFP gene between the env and the nef region. After transfection, cells containing pSUMA-EGFP showed strong green fluorescence. The result indicated that the inserted EGFP could be successfully expressed. Next, we infected TZM-b1 cell with pSUMA-EGFP-derived virus. A comparable infectivity to that of wild-type HIV-1 was observed. These results indicated that a large gene could be inserted between env and nef with no apparent effects on virus replication and infection.

pSUMA-AzFRS and pSUMA-TyrRS have been constructed and are evaluated, in the presence of a corresponding aminoacyl-tRNA synthetase, in humanized-BLT mice.

Example 15

HIV Containing Two Amber Mutations

To examine if the suppression of two amber codons on the HIV-1 genome by the $tRNA^{Tyr}$-AzFRS pair is sufficiently attenuated but still able to efficiently produce meaningful amounts of live HIV, an HIV-1 mutant was constructed having two amber mutations, Trp36 and Gln127 within the matrix domain (MA) of the Gag protein (pSUMA-Trp36Gln127). The positions were selected using the crystal structure of the MA protein (see PDB: 2H3F) and because they are not key residues for MA's interaction with phosphatidylinositol 4,5-bisphosphate. In addition, these mutation sites are located relative early on the HIV-1 genome, which reduces the chance of interference with the alternative reading frame and post-translational processing of the HIV proteins. Encouragingly, similar infection activity was observed with pSUMA-Trp36Gln127 (FIG. 5C) compared to an HIV-1 containing a single amber mutation (FIG. 5B). As a control, no live pSUMA-Trp36Gln127 virus was produced in the absence of AzF during viral assembly in 293T cells according to the infection assay (FIG. 8D).

Example 16

Light-Activated Replication of HIV-1

To add an additional regulatory element to control HIV-1 replication, HIV-1 mutants were generated that only replicate in the presence of 365 nm UV light. As shown in FIG. 10, an essential tyrosine or lysine residue in an HIV-1 protein is genetically replaced with o-nitrobenzyl-O-tyrosine (ONBY) or o-nitrobenzyl-oxycarbonyl-Nε-L-lysine (ONBK), respectively. With exposure to UV light, ONBY or ONBK is converted back to tyrosine or lysine, respectively, and the function of the protein is restored.

To examine the fidelity and efficiency of the genetic incorporation of ONBY and ONBK, the expression level of EGFP-Y39TAG, which contains an amber codon at position 39, was examined. As shown in FIG. 11, strong green fluorescence was only observed in samples supplemented with ONBY (FIG. 10A) or ONBK (FIG. 10C). Extremely weak signals were detected in samples without unnatural amino acids, which indicated an acceptable fidelity and efficiency.

Next, HIV-1 viability was tested after UV treatment. After being exposed to 365 nm UV light for 0, 5, 10, 20, or 30 minutes, HIV-1 viruses ware applied to TZM-b1 cells and the infectivity of the viruses were examined No obvious detrimental effects were observed for the UV-treated samples compared with non-treated control (0 minute sample). It was concluded that 365 nm UV light does not reduce virus infectivity.

ONBY and ONBK have been successfully incorporated into essential HIV-1 proteins, including the group specific antigen (Gag) and the protease.

Example 17

In Vivo Control of HIV Replication in a Humanized Mouse

To evaluate the live, attenuated HIV vaccine, the in vivo replication capacity and kinetics of the vaccine are examined in humanized mice (hu-BLT mice). The Hu-BLT mouse can reconstitute all major human hematopoietic lineages, including CD4+, CD8+T, B, monocyte/macrophage, dendritic and natural killer cells in both mucosal and secondary lymphatic tissues. Hu-BLT mice are generated from 6-8 week old female NSG (NOD/scid-γcnull) mice (Stock Number 005557, Jackson lab).

Three groups of hu-BLT mice (n=5) are exposed to a) wild-type pSUMA, b) pSUMA-tRNA-aaRS-Trp36Gln127 (a pSUMA-Trp36Gln127 variant that contains a genomic copy of suppressor tRNA and the corresponding aminoacyltRNA synthetase genes) with UAA*, or c) pSUMA-tRNA-aaRS-Trp36Gln127 without UAA*, and examined After intraperitoneal (i.p.) inoculation of virus at $1.0 \times 10^5$ TCID$_{50}$, UAA* is administered intraperitoneally to hu-BLT mice in the "pSUMA-tRNA-aaRS-Trp36Gln127 with UAA group". The plasma viral load of HIV-1 RNA in mice is monitored using real time qRT-PCR assay to determine if replication of pSUMA-tRNA-aaRS-Trp36Gln127 is tightly controlled with the availability of UAA*. The wild-type pSUMA is used as a positive control.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A live, attenuated human immunodeficiency virus (HIV), wherein a genome of the HIV comprises at least one mutation in an essential region, wherein the mutation is a nonsense mutation encoding a unnatural amino acid, wherein the unnatural amino acid is photoreactive, wherein the mutation is in a gag gene or a protease gene, and wherein the mutation is a substitution of a tyrosine residue or a lysine residue.

2. The live, attenuated HIV of claim 1, wherein the HIV is HIV-1, and wherein the mutation is at residue 59 of the HIV-1 protease gene.

3. The live, attenuated HIV of claim 1, wherein the genome of the HIV further comprises at least one transgene in a non-essential region, the transgene encoding a suppressor tRNA and a corresponding aminoacyl-tRNA synthetase.

4. The live, attenuated HIV of claim 3, wherein the non-essential region is between the env gene and the nef gene.

5. The live, attenuated HIV of claim 1, wherein the photoreactive amino acid is a photocaged amino acid.

6. The live, attenuated HIV of claim 5, wherein the photocaged amino acid is selected from the group consisting of o-nitrobenzyl-oxycarbonyl-Nε-L-lysine (ONBK) and o-nitrobenzyl-O-tyrosine (ONBY).

7. The live, attenuated HIV of claim 1, wherein the mutation is at residue 132 of the gag gene.

8. A method of making a live, attenuated HIV, comprising:

infecting a host cell with the live, attenuated HIV of claim 1; and purifying the live, attenuated HIV.

9. The method of claim 8, further comprising exposing the infected host cell to light.

10. The method of claim 9, wherein the light is UV light.

11. The method of claim 10, wherein the UV light is 365 nm light.

12. The method of claim 8, wherein the host cell comprises at least one transgene encoding a suppressor tRNA and a corresponding aminoacyl-tRNA synthetase.

13. An article of manufacture for producing a live, attenuated HIV, comprising:

the live, attenuated HIV of claim 1; and at least one unnatural amino acid (UAA*).

14. The article of manufacture of claim 13, further comprising a host cell.

15. The article of manufacture of claim 14, wherein the host cell comprises at least one transgene encoding a first suppressor tRNA and a first corresponding aminoacyl-tRNA synthetase pair that recognizes the unnatural amino acid.

16. The article of manufacture of claim 15, further comprising a photoreactive amino acid.

17. The article of manufacture of claim 13, wherein the UAA* is a photoreactive amino acid.

18. The article of manufacture of claim 16, wherein the host cell further comprises at least one transgene encoding a second suppressor tRNA and a second corresponding aminoacyl-tRNA synthetase pair that recognizes the photoreactive amino acid.

* * * * *